US00PP20701P2

(12) United States Plant Patent
Gilford et al.

(10) Patent No.: US PP20,701 P2
(45) Date of Patent: Feb. 2, 2010

(54) STRAWBERRY PLANT NAMED 'DRISSTRAWSIX'

(50) Latin Name: *Fragaria×Ananassa*
Varietal Denomination: DrisStrawSix

(75) Inventors: Kristie L. Gilford, Dover, FL (US); Philip J. Stewart, Watsonville, CA (US); Esther J. Pullen, Valrico, FL (US)

(73) Assignee: Driscoll Strawberry Associates, Inc., Watsonville, CA (US)

( * ) Notice: Subject to any disclaimer, the term of this patent is extended or adjusted under 35 U.S.C. 154(b) by 0 days.

(21) Appl. No.: 12/287,207

(22) Filed: Oct. 7, 2008

(51) Int. Cl.
*A01H 5/00* (2006.01)

(52) U.S. Cl. ..... Plt./208

(58) Field of Classification Search ..... Plt./208
See application file for complete search history.

*Primary Examiner*—Susan B McCormick Ewoldt
(74) *Attorney, Agent, or Firm*—Jondle & Associates, P.C.

(57) ABSTRACT

This invention relates to a new and distinct cultivar of strawberry plant named 'DrisStrawSix'. A new cultivar primarily characterized by its medium to large, sweet tasting fruit, early flowering and early harvest maturity, is disclosed.

3 Drawing Sheets

Genus and species: *Fragaria×ananassa.*
Variety denomination: 'DrisStrawSix'.

BACKGROUND OF THE NEW PLANT

The present invention relates to a new and distinct strawberry cultivar designated 'DrisStrawSix' and botanically known as *Fragaria×ananassa*. This new strawberry cultivar was discovered in Hillsborough, Fla. in December, 2002 and originated from a cross between the female proprietary parent '74G14' (unpatented) and the male proprietary parent '6F-158' (unpatented). The original seedling of the new cultivar was asexually propagated at a nursery in Shasta County, Calif. 'DrisStrawSix' was subsequently asexually propagated and underwent further testing at a nursery in Hillsborough, Fla. for five years. The present invention has been found to retain its distinctive characteristics through successive asexual propagations.

DESCRIPTION OF THE PHOTOGRAPHS

The accompanying color photographs show typical specimens of the new cultivar at various stages of development as nearly true as it is possible to make in color reproductions.

DESCRIPTION OF THE NEW CULTIVAR

Figure 1:
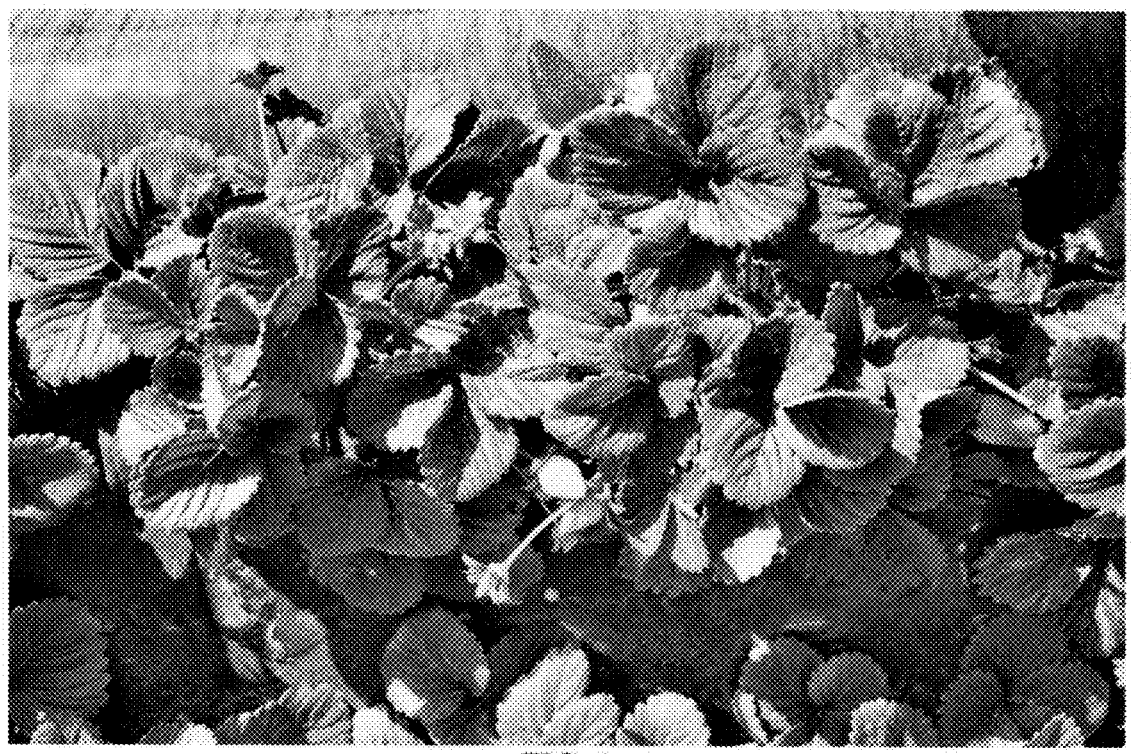
FIG. 1 shows overall plant habit including fruit at various stages of development.
Figure 2:
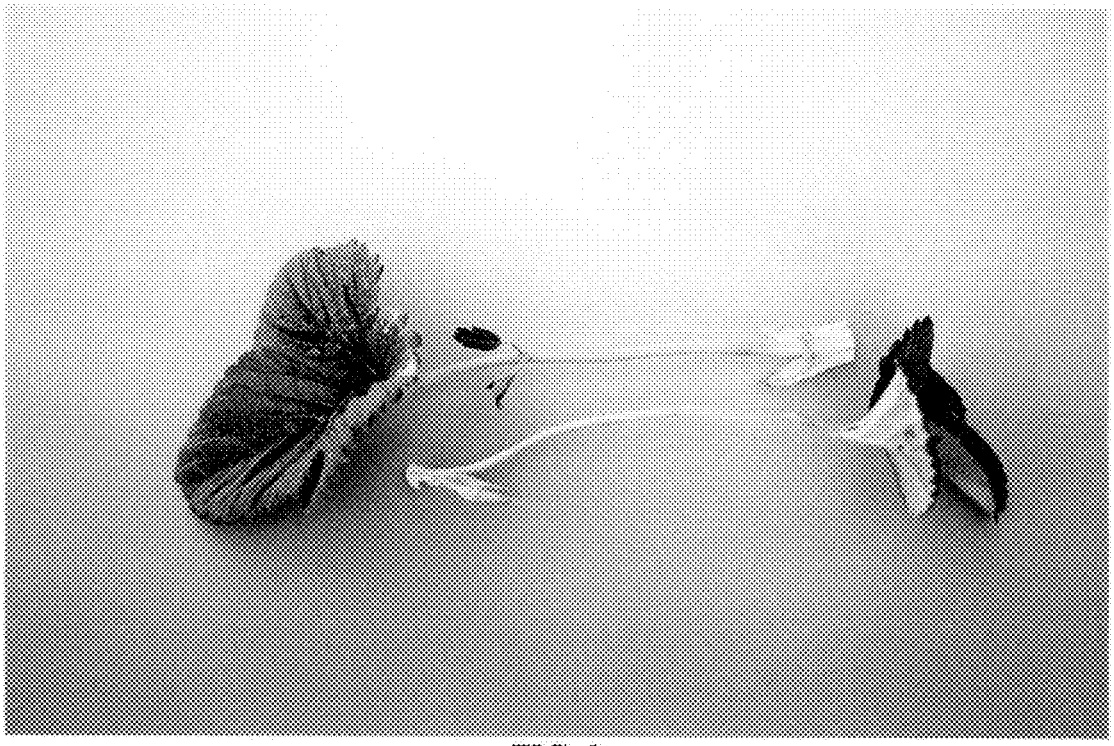
FIG. 2 shows leaves of the plant with three leaflets.
Figure 3:
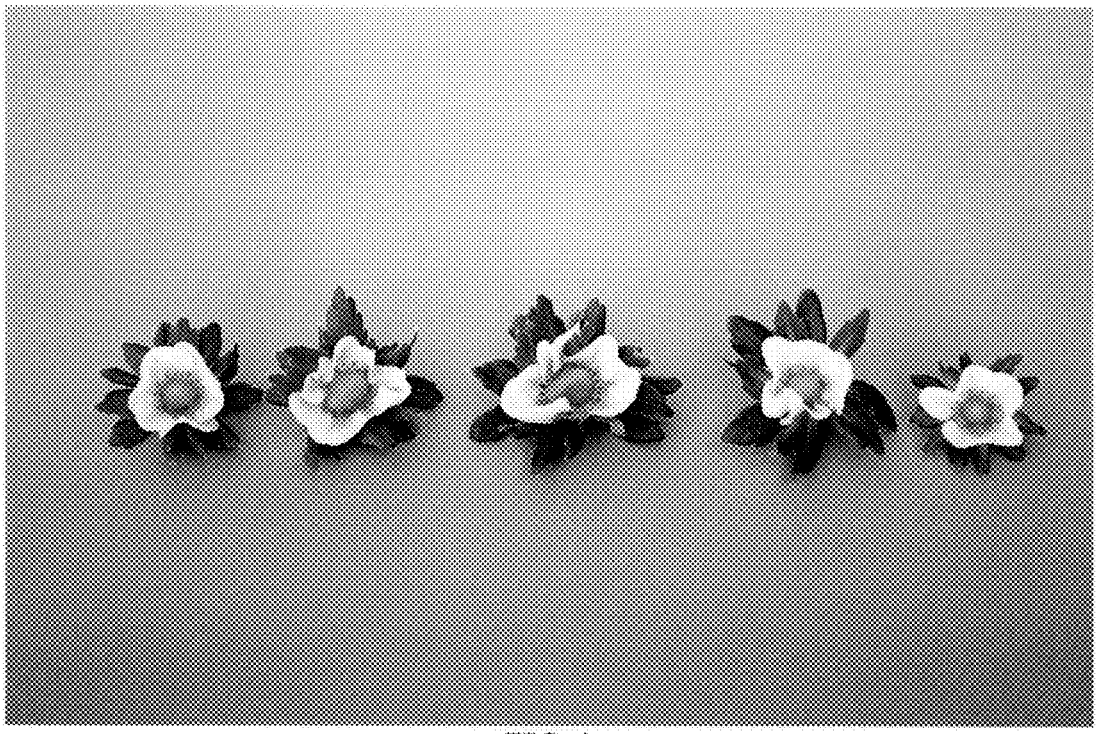
FIG. 3 shows the upperside of several of the flowers.
Figure 4:
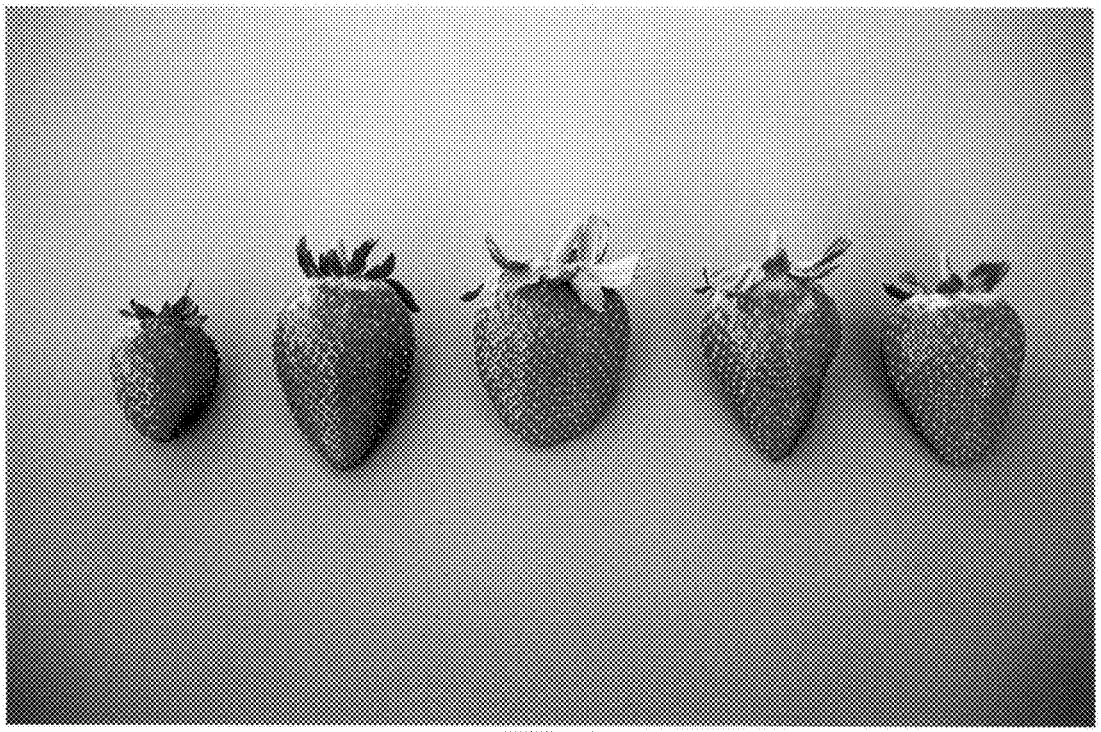
FIG. 4 shows the whole fruit.
Figure 5:
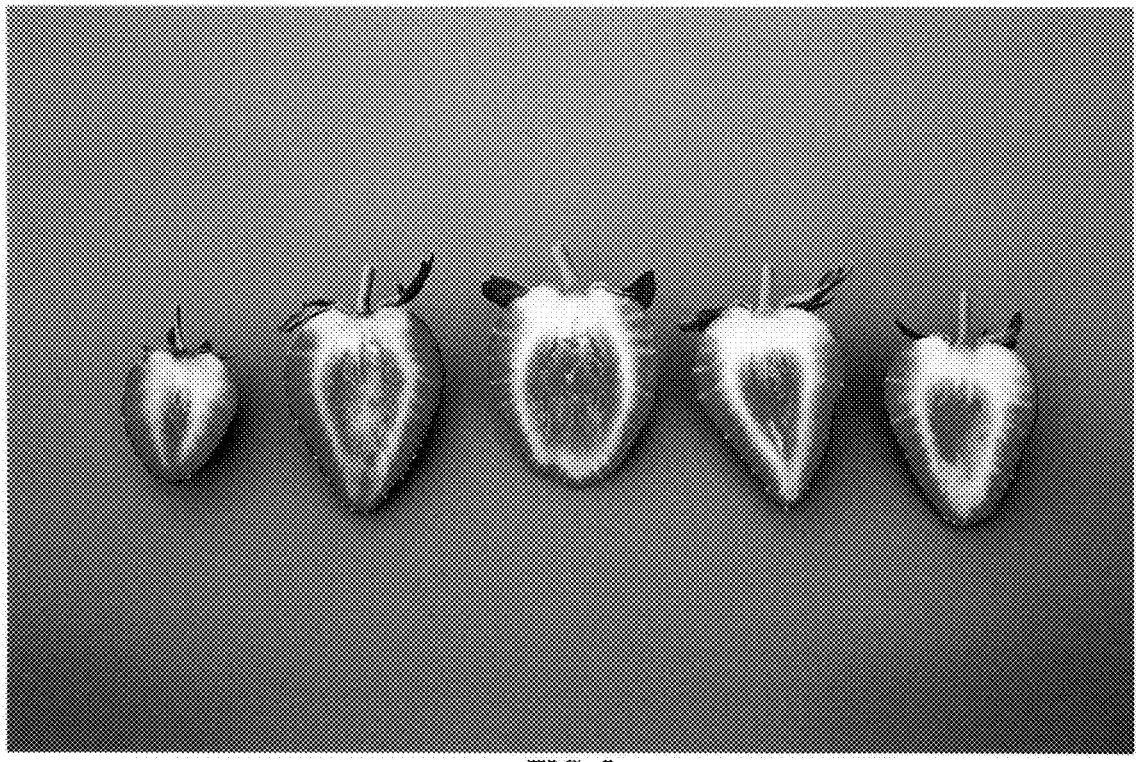
FIG. 5 shows the fruit in longitudinal cross-section.

The following description of 'DrisStrawSix' is based on observations taken from the 2003 to 2008 growing seasons in Hillsborough, Fla. This description is in accordance with UPOV terminology. Color designations, color descriptions, and other phenotypical descriptions may deviate from the stated values and descriptions depending upon variation in environmental, seasonal, climatic and cultural conditions. 'DrisStrawSix' has not been observed under all possible environmental conditions. Color terminology follows The Royal Horticultural Society Colour Chart, London (R.H.S.) (2001).

COMPARISON WITH PARENTAL LINES

'DrisStrawSix' is distinguished from its parents '74G14' or '6F158' mainly by yield and fruit size. 'DrisStrawSix' has a significantly higher yield than either '74G14' or '6F158'. Additionally, 'DrisStrawSix' has a fruit size that is thirty percent larger than either '74G14' or '6F158'.

DETAILED BOTANICAL DESCRIPTION

Table 1 shows plant characteristics of the new variety compared with plant characteristics of the commercial varieties 'Driscoll Atlantis' (U.S. Plant Pat. No. 16,475) and 'Driscoll Sanibel' (U.S. Plant Pat. No. 16,298). Plant characteristics include plant height, diameter, number of crowns per plant, habit, density of individual plant and vigor.

TABLE 1

| Characteristic | 'DrisStrawSix' | 'Driscoll Atlantis' | 'Driscoll Sanibel' |
|---|---|---|---|
| Plant height (cm) | 21.3 | 19.8 | 20.2 |
| Plant diameter (cm) | 44.0 | 38.9 | 38.7 |
| Number of crowns/plant | 4 | 3 | 2 |
| Habit | Flat globose | Flat globose | Flat |
| Density of individual plant | Medium | Between medium and dense | Medium |
| Vigor | Between medium and strong | Medium | Strong |

Table 2 shows leaf characteristics of the new cultivar compared with leaf characteristics of 'Driscoll Atlantis' and 'Driscoll Sanibel'. Leaf characteristics include terminal leaflet length and width in centimeters, length to width ratio, number of teeth per terminal leaflet, shape of teeth, color of upperside and underside of leaf, leaf shape in cross section, leaf blistering, leaf glossiness, number of leaflets, terminal leaflet margin, terminal leaflet length to width ratio, shape of the leaflet, shape of the leaf apex and shape of leaf base.

TABLE 2

| Leaf Characteristic | 'DrisStrawSix' | 'Driscoll Atlantis' | 'Driscoll Sanibel' |
|---|---|---|---|
| Terminal leaflet length (cm) | 8.35 | 7.89 | 8.56 |
| Terminal leaflet width (cm) | 8.16 | 8.01 | 8.47 |
| Terminal leaflet length/width ratio | 1.0 | 1.0 | 1.0 |
| No. teeth/terminal leaflet | 20 | 23 | 22 |
| Shape of teeth | Between obtuse and rounded | Between obtuse and rounded | Rounded |
| Color of upperside of leaf | RHS 137B Dark green | RHS 137A Dark green | RHS 131B Dark green |
| Color of underside of leaf | RHS 138B Medium green | RHS 140D Light green | RHS 142C Light green |
| Leaf shape in cross section | Between slightly concave and flat | Between slightly concave and flat | Slightly concave |
| Leaf blistering | Medium | Medium | Between medium and strong |
| Leaf glossiness | Medium | Weak | Medium |
| No. leaflets | Three only | Three only | Three only |
| Terminal leaflet margin | Revolute | Flat | Flat |
| Terminal leaflet: length/width ratio | As long as broad | As long as broad | As long as broad |
| Terminal leaflet shape | Orbicular | Ovate | Between oval and ovate |
| Terminal leaflet base shape | Slightly oblique | Not available | Obtuse |
| Terminal leaflet apex shape | Rounded | Rounded | Rounded |

Table 3 shows information about the petiole, the petiolule, the bract, and the stipule of the new cultivar compared to 'Driscoll Atlantis' and 'Driscoll Sanibel'. This includes petiole length in centimeters, petiole diameter in centimeters, petiole pubescence, pose of hairs on the petiole, color of the petiol, color of the petiolule, petiolule length in centimeters, petiolule diameter in centimeters, bract frequency per petiole, stipule length in centimeters, stipule width in centimeters, and stipule pubescence.

TABLE 3

| Characteristic | 'DrisStrawSix' | 'Driscoll Atlantis' | 'Driscoll Sanibel' |
|---|---|---|---|
| Petiole length (cm) | 13.4 | 13.7 | 15.3 |
| Petiole diameter (cm) | 0.383 | 0.430 | 0.455 |
| Petiole pubescence | Medium | Dense | Medium |
| Petiole pose of hairs | Outwards | Outwards | Between outwards and downwards |
| Petiole color | RHS 145B Light yellow-green | RHS 145C Light yellow-green | RHS 145D Light yellow-green |
| Petiolule color | RHS 145B Light yellow-green | RHS 145C Light yellow-green | RHS 145D Light yellow-green |
| Petiolule length (cm) | 1.208 | 1.451 | 1.626 |

TABLE 3-continued

| Characteristic | 'DrisStrawSix' | 'Driscoll Atlantis' | 'Driscoll Sanibel' |
|---|---|---|---|
| Petiolule diameter (cm) | 0.200 | 0.213 | 0.233 |
| Bract frequency | 1 | 2 | 2 |
| Stipule length (cm) | 4.1 | 3.7 | 3.9 |
| Stipule width (cm) | 0.096 | 0.087 | 0.112 |
| Stipule pubescence | Medium | Dense | Medium |
| Stipule anthcyanin coloration | Weak | | |

Table 4 shows stolon characteristics of the new cultivar compared to 'Driscoll Atlantis' and 'Driscoll Sanibel'. These characteristics include the number of stolons, average number of daughter plants, the anthocyanin coloration of the stolons, the thickness of the stolons, and the pubescence of the stolons.

TABLE 4

| Characteristic | 'DrisStrawSix' | 'Driscoll Atlantis' | 'Driscoll Sanibel' |
|---|---|---|---|
| Stolon Number | Many | | |
| Average number of daughter plants | 50 | 53 | 52 |
| Stolon Anthocyanin | Strong | Between weak and medium | Strong |
| Stolon Thickness | Medium | Medium | Medium |
| Stolon Pubescence | Dense | Medium | Medium |

Table 5 shows inflorescence characteristics of the new cultivar compared to 'Driscoll Atlantis' and 'Driscoll Sanibel'. These characteristics include inflorescence position relative to foliage, relative flower size, flower diameter in centimeters (measured from petal tip to petal tip), petal shape, petal spacing (relative spacing of petals), petal apex shape, petal margin, petal base shape, petal length in centimeters, petal width in centimeters, petal length to width ratio, typical and observed number of petals, petal color, calyx diameter in centimeters (measured on back of flower from sepal tip to sepal tip), diameter of calyx relative to corolla, diameter of inner calyx relative to outer, sepal shape, sepal apex shape, sepal margin, sepal length in centimeters (measured from sepal tip to point of attachment to receptacle), sepal width in centimeters, typical and observed number of sepals, receptacle color and anther color.

TABLE 5

| Characteristic | 'DrisStrawSix' | 'Driscoll Atlantis' | 'Driscoll Sanibel' |
|---|---|---|---|
| Inflorescence position relative to foliage | Above | Between level with and above | Between beneath and level with |
| Flower size | Between small and medium | Between medium and large | Large |
| Flower diameter (cm) | 2.075 | 2.369 | 2.070 |

TABLE 5-continued

| Characteristic | 'DrisStrawSix' | 'Driscoll Atlantis' | 'Driscoll Sanibel' |
|---|---|---|---|
| Petal shape | Orbicular | Orbicular | Orbicular |
| Petal spacing | Overlapping | Overlapping | Between touching and overlapping |
| Petal apex shape | Rounded | Rounded | Rounded |
| Petal margin | Entire | Entire | Entire |
| Petal base shape | Concavo-convex | Rounded | Rounded |
| Petal length (cm) | 1.252 | 1.248 | 1.166 |
| Petal width (cm) | 1.322 | 1.302 | 1.188 |
| Petal length/width ratio | As long as broad | As long as broad | As long as broad |
| Petal length/width ratio | 0.9 | 1.0 | 1.0 |
| Typical and observed petal number | 6 | 5 | 6 |
| Petal color | RHS 155C White | RHS 155C White | RHS 155C White |
| Calyx diameter (cm) | 3.304 | 2.871 | 2.997 |
| Calyx diameter relative to corolla | Between same size and larger | Between same size and larger | Between same size and larger |
| Inner calyx diameter relative to outer | Between smaller and same size | Same size | Larger |
| Sepal shape | Elliptical | Elliptical | Elliptical |
| Sepal apex shape | Convex | Convex | Convex |
| Sepal margin | Entire | Entire | Entire |
| Sepal length (cm) | 1.200 | 1.040 | 1.172 |
| Sepal width (cm) | 0.660 | 0.713 | 0.637 |
| Typical and observed sepal number | 11 | 11 | 11 |
| Receptacle color | RHS 4A Medium yellow | RHS 149A Dark yellow-green | RHS 149B Dark yellow-green |
| Anther color | RHS 13A Dark yellow | RHS 9A Dark yellow | RHS 9A Dark yellow |

Table 6 shows fruit characteristics of the new cultivar compared to 'Driscoll Atlantis' and 'Driscoll Sanibel'. These characteristics include fruiting truss length and diameter in centimeters, number of berries per fruiting truss, fruiting truss attitude, fruiting truss length, fruit length in centimeters, fruit width in centimeters, fruit length to width ratio, fruit hollow length and width in centimeters, fruit hollow length to width ratio, fruit weight in grams, relative fruit size, predominant fruit shape, difference in shape between primary and secondary fruits, band without achenes, unevenness of fruit surface, fruit skin color, evenness of fruit color, fruit glossiness, insertion of achenes, achene coloration (sunward and shaded sides of berry), insertion of calyx, pose of calyx segments, size of calyx in relation to fruit, adherence of calyx, firmness of flesh, color of the fruit flesh, evenness of the flesh color, distribution of flesh color, relative size of hollow center, sweetness of fruit, acidity of fruit, texture of fruit when tasted, time of flowering, harvest maturity, type of bearing, grams of fruit per plant.

TABLE 6

| Characteristic | 'DrisStrawSix' | 'Driscoll Atlantis' | 'Driscoll Sanibel' |
|---|---|---|---|
| Fruiting truss length (cm) | 25.2 | 22.7 | 19.7 |
| Fruiting truss diameter (cm) | 0.336 | 0.423 | 0.404 |
| Number of berries per fruiting truss | 1 | 3 | 1 |
| Fruiting truss attitude | Prostrate | Prostrate | Prostrate |
| Fruiting truss length | Between medium and long | Medium | Medium |
| Fruit length (cm) | 5.410 | 4.200 | 5.180 |
| Fruit width (cm) | 4.130 | 3.640 | 4.610 |
| Fruit length/width ratio | 1.3 | 1.2 | 1 .1 |
| Fruit length/width ratio | Longer than broad | Longer than broad | Longer than broad |
| Fruit hollow length (cm) | 3.050 | 1.880 | 2.310 |
| Fruit hollow width (cm) | 0.770 | 0.850 | 0.790 |
| Fruit hollow length/width ratio | 4.0 | 2.2 | 2.9 |
| Fruit weight (g) | 29.9 | 23.8 | 31.8 |
| Relative fruit size | Between medium and large | Medium | Between large and very large |
| Predominant fruit shape | Conical | Conical | Conical |
| Difference in shape between primary & secondary fruits | Slight | Slight | Slight |
| Band without achenes | Narrow | Absent or very narrow | Narrow |
| Unevenness of fruit surface | Between weak and medium | Between weak and medium | Medium |
| Fruit skin color | RHS 46B Medium red | RHS 45B Medium red | RHS 43A Medium red |
| Evenness of fruit color | Slightly uneven | Even | Even |
| Fruit glossiness | Strong | Strong | Strong |
| Insertion of achenes | Level with surface | Level with surface | Level with surface |
| Achene coloration sunward side of berry | RHS 30A Medium red | RHS 185D Greyed-purple | RHS 182A Medium greyed-red |
| Achene coloration shaded side of berry | RHS 151D Light yellow-green | RHS 151D Light yellow-green | RHS 150C Light yellow-green |
| Insertion of calyx | Level | Level | Level |
| Pose of calyx segments | Between spreading and reflexed | Between spreading and reflexed | Between spreading and reflexed |
| Size of calyx in relation to fruit | Larger | Between same size and larger | Larger |
| Adherence of calyx | Strong | Strong | Strong |
| Firmness of flesh | Medium | Firm | Medium |
| Color of the flesh | RHS 43B Medium red | RHS 42B Medium red | RHS 40C Medium red |
| Evenness of flesh color | Slightly uneven | Slightly uneven | Slightly uneven |
| Distribution of flesh color | Only marginal | Marginal and central | Marginal and central |
| Hollow center | Small | Medium | Medium |
| Sweetness | Strong | Strong | Strong |
| Acidity | Medium | Medium | Medium |

TABLE 6-continued

| Characteristic | 'DrisStrawSix' | 'Driscoll Atlantis' | 'Driscoll Sanibel' |
|---|---|---|---|
| Texture when tasted | Between fine and medium | Medium | Fine |
| Time of flowering | Early | Very early | Early |
| Harvest maturity (50% of plants with ripe fruit) | Early December to late April | Late November to mid-March | Late November to mid-March |
| Type of bearing | Not everbearing | Partially everbearing | Partially everbearing |
| Grams of fruit/plant | 568 | 360 | 448 |

Table 7 shows pest and disease characteristics of the new cultivar compared to 'Driscoll Atlantis' and 'Driscoll Sanibel'.

TABLE 7

| Pest or Disease | 'DrisStrawSix' | 'Driscoll Atlantis' | 'Driscoll Sanibel' |
|---|---|---|---|
| *Xanthomonas fragarie* | Susceptible | Moderately susceptible | Moderately susceptible |

We claim:

1. A new and distinct cultivar of strawberry plant, as described and shown herein.

* * * * *